United States Patent [19]

Gonzalez

[11] Patent Number: 5,313,939
[45] Date of Patent: May 24, 1994

[54] ENDOTRACHEAL TM TUBE FOR TOPICAL SUBSTANCE DELIVERY AND ASSOCIATED METHOD OF USE

[75] Inventor: René M. Gonzalez, Pittsburgh, Pa.

[73] Assignee: University of Pittsburgh of the Commonwealth System of Higher Education, Pittsburgh, Pa.

[21] Appl. No.: 775,721

[22] Filed: Oct. 11, 1991

[51] Int. Cl.⁵ .................. A61M 16/10; A61M 15/00; A61M 11/00; A62B 9/06
[52] U.S. Cl. .................. 128/207.14; 128/203.12; 128/200.14; 604/28; 604/49; 604/54; 604/181; 604/187
[58] Field of Search .............. 128/200.14, 200.24, 128/200.26, 203.12, 207.14, 207.15, 207.16, 911, 912; 604/93, 96, 49, 97, 102, 112, 151, 132, 181, 187, 191, 264, 28, 54

[56] References Cited

U.S. PATENT DOCUMENTS

| | | |
|---|---|---|
| 3,173,418 | 3/1965 | Baran . |
| 3,394,705 | 7/1968 | Abramson . |
| 3,593,713 | 7/1971 | Bogoff . |
| 4,156,428 | 5/1979 | Henkin ............................ 128/207.16 |
| 4,230,108 | 10/1980 | Young ............................ 128/207.15 |
| 4,327,721 | 5/1982 | Goldin et al. ................... 128/207.15 |
| 4,405,308 | 9/1983 | Jessup ............................ 128/207.14 |
| 4,501,580 | 2/1985 | Glassman ........................ 604/43 |
| 4,584,998 | 4/1986 | McGrail .......................... 128/207.15 |
| 4,632,108 | 12/1986 | Geil .............................. 128/207.15 |
| 4,669,463 | 6/1987 | McConnell ...................... 128/207.14 |
| 4,693,243 | 9/1987 | Buras ............................ 128/207.15 |
| 4,739,756 | 4/1988 | Horn ............................. 128/207.16 |
| 4,977,894 | 12/1990 | Davies ........................... 128/207.15 |
| 5,031,613 | 7/1991 | Smith et al. .................... 128/207.15 |
| 5,146,916 | 9/1992 | Catalani ......................... 128/207.15 |

FOREIGN PATENT DOCUMENTS 3918956 12/1989 Fed. Rep. of Germany ...................... 128/207.14

Primary Examiner—Edgar S. Burr
Assistant Examiner—Kimberly L. Asher
Attorney, Agent, or Firm—Arnold B. Silverman; George K. Stacey

[57] ABSTRACT

An apparatus for topical targeted delivery of a substance to generally the entire or selected portions of the internal body tissues and walls of a tracheal-intubated patient's upper airway is disclosed. The apparatus includes a tube member for ventilating or oxygenating a patient's lungs that has an annular inner surface, an annular outer surface having a plurality of opening extending over a major portion of the axial extent of the annular outer surface, and at least one first conduit member that is positioned generally at least in part between the annular inner surface and the annular outer surface. The first conduit member extends over the major portion of the axial extent of the annular outer surface of the tube member. The first conduit member has a plurality of perforations in alignment with the openings of the annular outer surface for effecting delivery of the substance to the surrounding internal body tissues and walls of the patient's upper airway. A method for delivering the substance to generally the entire or selected portions of the mucosal lining and anatomical structures of the patient's upper airway employing this apparatus is disclosed.

42 Claims, 4 Drawing Sheets

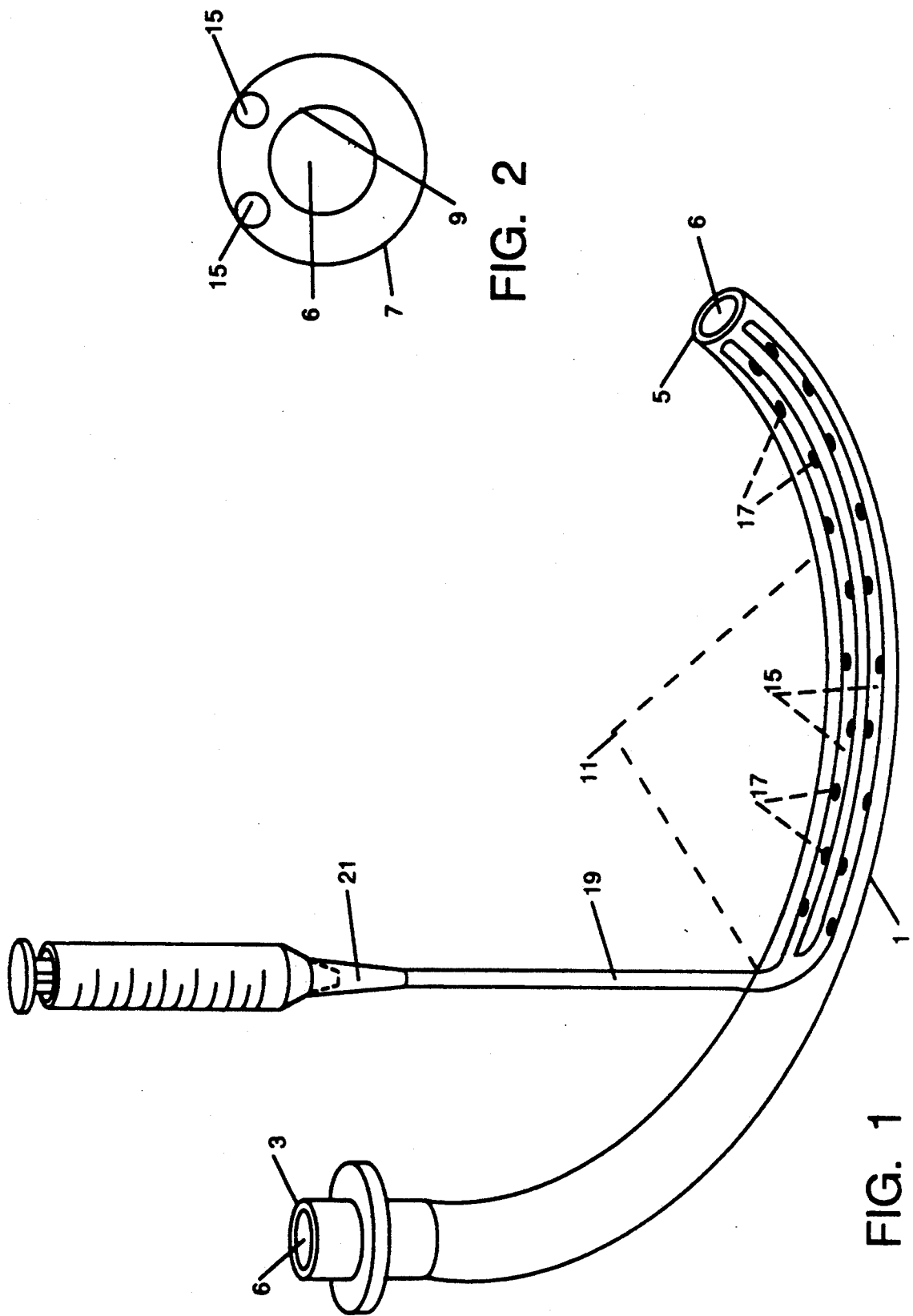

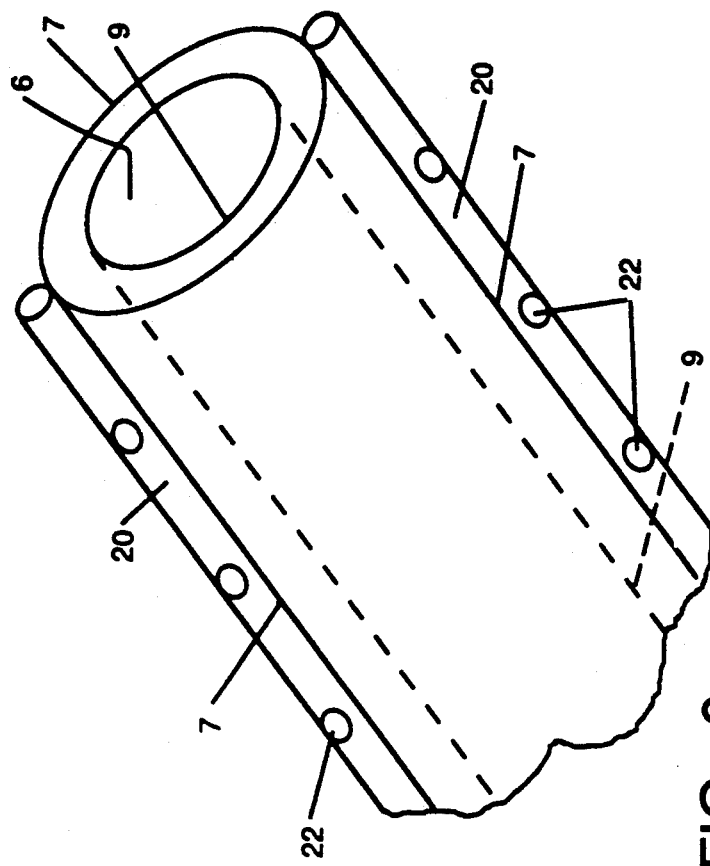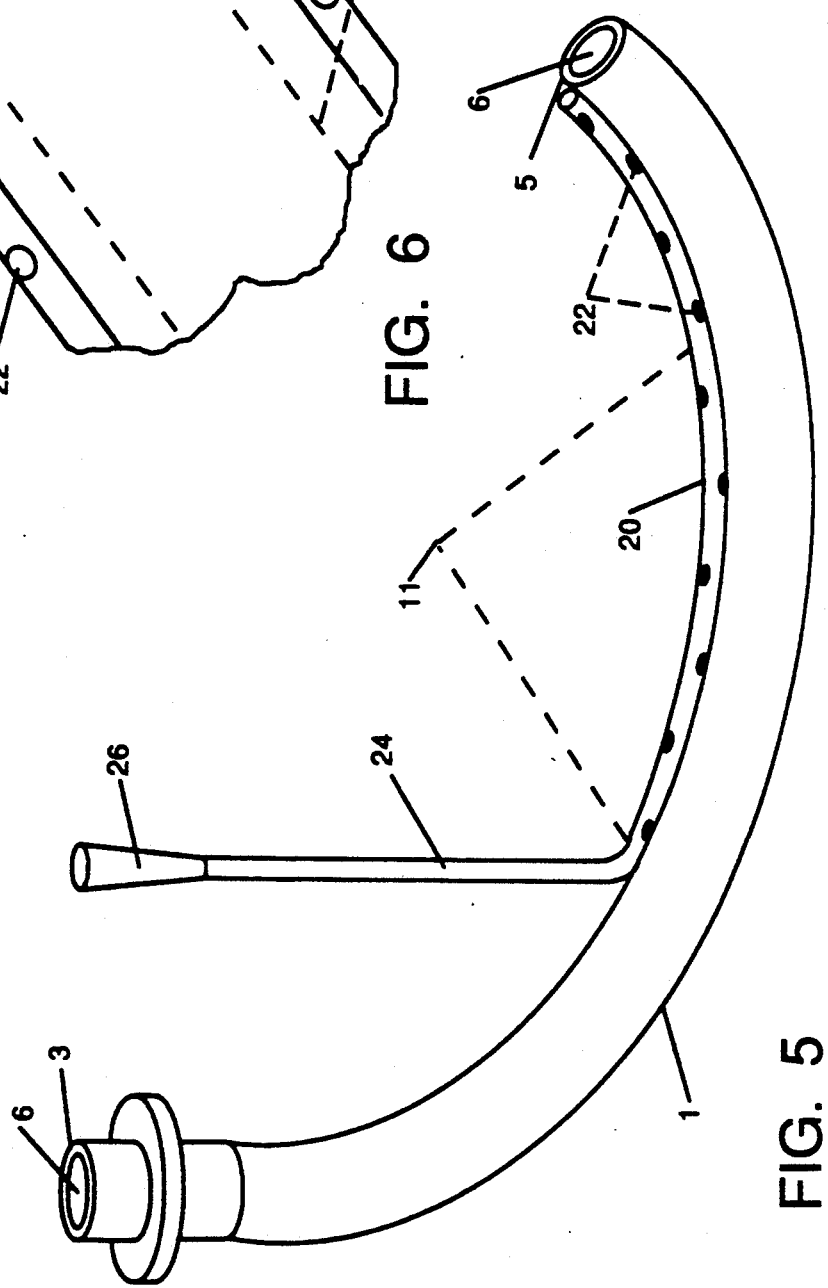

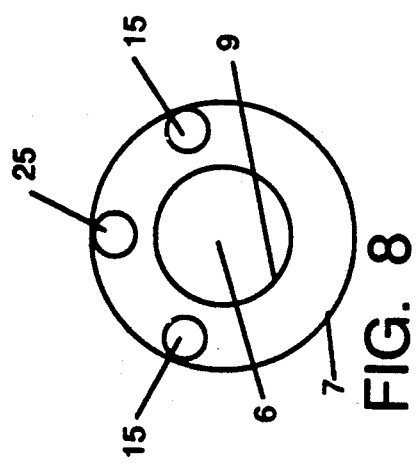
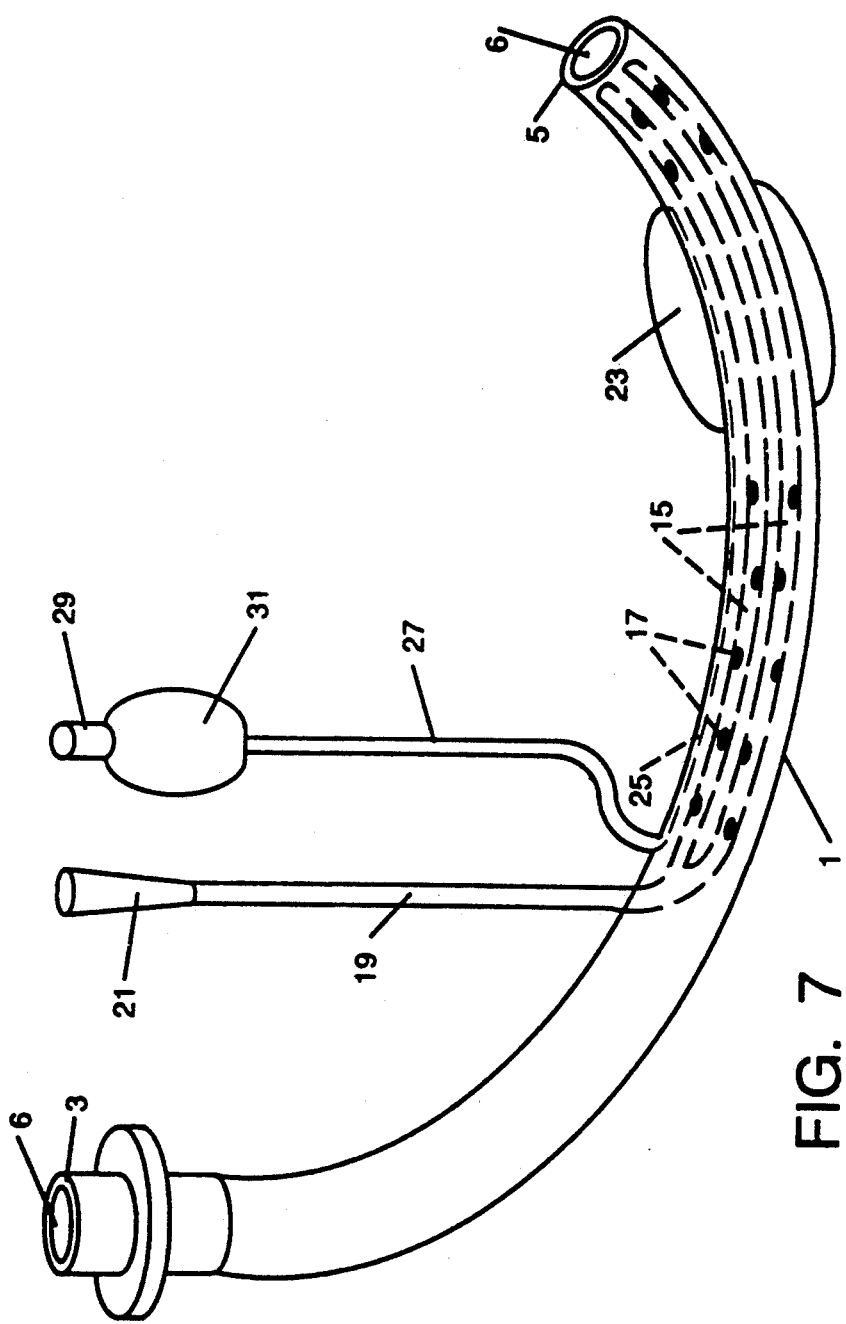
FIG. 8
FIG. 7

ENDOTRACHEAL TM TUBE FOR TOPICAL SUBSTANCE DELIVERY AND ASSOCIATED METHOD OF USE

BACKGROUND OF THE INVENTION

1. Field of the Invention

This invention relates to an apparatus and a method for the topical targeted delivery of a substance to the internal body tissues and walls of a patient's upper airway.

2. Brief Description of the Prior Art

The endotracheal tube and the tracheostomy tube are life-support devices commonly used to secure and protect the upper airway of a patient and to permit safe and proper life-sustaining ventilation and oxygenation of a patient's lungs. An endotracheal tube is made of any suitable material such as, for example, a resinous plastic material, metal or rubber and may be made of an opaque, translucent or transparent material. The material may be flexible or rigid. Endotracheal tubes may be manufactured using extrusion or other techniques well known by those skilled in the art. Generally, an endotracheal tube is placed through a patient's nose or mouth and down into the trachea (windpipe). A tracheostomy tube is similar in design and function to an endotracheal tube, however, the major difference being that a tracheostomy tube is shorter in length and is placed by way of a surgical incision in the patient's neck directly into the larynx (voicebox) or trachea.

Endotracheal and tracheostomy tubes are used throughout the world in a variety of clinical settings, including for example, patients receiving general anesthesia and critically ill patients requiring life-support. Several problems and potential hazards, however, are associated with the use of endotracheal or tracheostomy tubes. One important problem associated with these tubes is that they are irritating to the unanesthetized mucosal lining of the nose, mouth, pharynx (throat), larynx and trachea. For this reason, these tubes can produce violent coughing and gagging when inserted into or when present in the upper airway of awake, semi-awake or lightly anesthetized patients. Coughing and gagging can lead to several undesirable and dangerous outcomes. The patient's violent movements associated with coughing and gagging can result in the patient inadvertently and prematurely coughing or pulling out the endotracheal tube, or in the patient pulling out the patient's intravenous lines or pulling off of vital monitors. The coughing may be so violent that it necessitates the anesthesia care team to prematurely remove the endotracheal or tracheostomy tube. This premature removal of the tube can lead to life-threatening or health-threatening conditions, such as for example, laryngospasm with accompanying total airway obstruction or aspiration of vomitus into the lungs. Additionally, violent coughing may threaten or damage delicate surgical repairs, such as for example, surgery on the tiny bones of the middle ear or on the fragile structures of the eye.

The irritating effect of the endotracheal tube or tracheostomy tube also frequently produces severe and life-threatening or health-threatening elevations in blood pressure, heart rate, intracranial pressure and life-threatening bronchospasm in patients with a history of asthma or other lung diseases. Another hazard of using endotracheal or tracheostomy tubes is that they can mechanically traumatize or abrade the sensitive mucosal lining of the upper airway during placement of the tube, particularly in patients in whom the tracheal intubation was technically difficult and required multiple attempts, or in patients requiring extended or prolonged tracheal intubation. This can lead to significant swelling and inflammation of the airway. Subsequent to the removal of the tube, this airway swelling or inflammation can lead to partial or substantially total airway obstruction resulting in damage to the brain or heart from insufficient oxygen.

A number of patents disclose endotracheal or tracheostomy tubes and methods for promoting ventilation or respiration, but none teach or suggest the improved results of the device and process of the present invention.

U.S. Pat. No. 4,327,721 discloses an endotracheal tube including an expandable cuff and an annular chamber circumferentially extending around the endotracheal tube. This patent states that the outer walls of the annular chamber have spaced openings through which topical agents are dispensed to the mucosal area of the trachea.

U.S. Pat. No. 3,173,418 discloses an endotracheal tube having an internal cuff and a multiperforated external cuff. This patent states that anesthetic fluid is injected into the space between the external and internal cuffs and is sprayed through the holes of the external cuff allowing anesthetic to be delivered around the surface of the external cuff to the mucous membranes of a patient's trachea.

U.S. Pat. No. 4,230,108 discloses a flexible esophageal tube having inflatable cuffs, and a ventilation tube. This patent states that the esophageal tube and the ventilation tube define common perforations in the area between the cuffs for ventilating the lungs.

In spite of these prior art disclosures, there remains a very real and substantial need for an apparatus and a method for improving a patient's tolerance of an endotracheal or tracheostomy tube in the patient's upper airway.

SUMMARY OF THE INVENTION

The present invention has met the above-described need. The apparatus and method of the present invention provide an efficient and economical approach for substantially reducing the undesired problems and hazards associated with endotracheal or tracheostomy tubes.

The apparatus of this invention provides for topical targeted delivery of a substance to the surrounding internal body tissues and walls of a patient's upper airway. This apparatus includes a tube member having (a) a proximal open end, a distal open end, and a central lumen that is disposed between the proximal open end and the distal open end, and (b) an annular outer surface having a plurality of openings, and an annular inner surface. The openings of the annular outer surface are distributed or extend over a portion of the axial extent of the annular outer surface of the tube member. A substance delivery means includes at least one conduit member disposed generally at least in part between the annular inner surface and the annular outer surface. The conduit member extends over a portion of the axial extent of the annular outer surface of the tube member. Preferably, the conduit member is positioned generally parallel to the longitudinal axis of the tube member. The conduit member has a plurality of perforations that are distributed or extend over the conduit member in substantial alignment with the openings of the annular outer surface of the tube member. This alignment of the conduit member perforations and the openings of the annular outer surface of the tube member allow for a substance to flow from within the conduit member by passing through the perforations of the conduit member and the openings of the tube member to the surrounding internal body tissues and walls of the patient's upper airway. At least one supply means communicates with at least one conduit member for transferring the substance to the conduit member. In one embodiment, conduit members of at least one supply means extend over a major and/or a minor portion of an axial extent of the tube member. In another embodiment, conduit members of at least one substance delivery means extend over a major portion of the axial extent of the tube member and conduit members of another substance delivery means extend over a minor portion of the axial extent of the tube member.

In another embodiment of this invention, the apparatus includes at least one passageway positioned on the annular outer surface of the tube member. In this embodiment the annular outer surface does not include openings. Passageways may extend over major and/or minor portions of the axial extent of the annular outer surface of the tube member. Preferably, each passageway is positioned generally parallel to the longitudinal axis of the tube member. Each passageway has a plurality of apertures that are distributed or extend over the passageway. The apertures allow a substance to flow from within the passageways through the apertures to the surrounding internal body tissues and walls of the patient's upper airway. At least one supply means communicates with at least one passageway for transferring the substance to the passageway. More than one passageway may be connected to each supply means.

In another embodiment of this invention, the apparatus further includes at least one inflatable balloon cuff member that is attached to and continuously encircles at least part of the axial extent of the tube member.

A method of the present invention provides for the topical targeted delivery of a substance to the mucosal lining and anatomical structures of a patient's upper airway that includes employing the apparatus of this invention, inserting at least part of the apparatus of this invention into a patient's upper airway, injecting a substance into at least one injection port which communicates with the supply means for the transfer of the substance through the supply means and into at least one conduit member, and effecting the flow of the substance through a plurality of the aligned conduit member perforations and the openings of the outer surface of the tube member for delivering the substance to generally the entire mucosal lining and anatomical structures of the patient's upper airway. Injecting substance into more than one injection port allows delivery of the substance to the patient's airway over major and/or minor axial portions of the axial extent of the apparatus.

Another method of this invention provides for the topical delivery of the substance to the patient's upper airway that includes employing the apparatus of this invention, inserting at least part of the apparatus of this invention into a patient's upper airway, injecting the substance into at least one injection port which communicates with at least one supply means for the transfer of the substance through the supply means and into at least one passageway. The passageway is disposed on the annular outer surface of the tube member. This method includes effecting the flow of the substance through a plurality of the apertures of the passageway for delivering the substance to the mucosal lining and anatomical structures of the patient's upper airway.

It is an object of the present invention to provide an apparatus and method for reducing the undesired problems and hazards associated with the use of endotracheal or tracheostomy tubes.

It is another object of the present invention to provide an apparatus for increasing a patient's tolerance to maintain a tracheostomy or endotracheal tube in the upper airway for ventilation and oxygenation of the lungs.

It is another object of this invention to provide a method for the topical targeted delivery of a substance to the mucosal lining and anatomical structures of a patient's upper airway.

These and other objects of the invention will be more fully understood from the following descriptions of the invention, the drawings and the claims appended hereto.

BRIEF DESCRIPTION OF THE DRAWINGS

FIG. 1 is a schematic perspective view of a form of the apparatus of this invention having a tube member and at least one first conduit member positioned generally at least in part between the annular inner surface and the annular outer surface of the tube member;

FIG. 2 is a cross-sectional view of the apparatus of FIG. 1 taken through line 2—2;

FIG. 5 is a schematic perspective of another embodiment of this apparatus including at least one passageway disposed on the annular outer surface of the tube member;

FIG. 6 is a schematic perspective of the apparatus of FIG. 5;

FIG. 7 is a schematic perspective view of another embodiment of this apparatus including at least one inflatable balloon cuff member that is attached to and continuously encircles at least part of the axial extent of the tube member; and FIG. 8 is a cross-sectional view of the apparatus of FIG. 7 taken through line 8—8.

DESCRIPTION OF THE PREFERRED EMBODIMENTS

As used herein, the term "patient" includes members of the animal kingdom including, but not limited to, human beings.

As employed herein, "substance" includes an agent, such as for example, a medication. The medication may be in a liquid or gaseous state. Examples of classes of medications include but are by no means limited to (1) local anesthetics, (2) anti-inflammatory drugs, such as for example, steroids, (3) antibiotics, (4) vasoconstrictive or sympathomimetic agents such as racemic epinephrine, (5) irrigants and (6) lubricants.

As used herein, the expression "major portion" shall mean from about 50 to 100 percent (%) of the axial extent of the annular outer surface of the tube member measured from the distal open end to the proximal open end of the tube member.

As used herein, the expression "minor portion" shall mean less than 50 percent of the axial extent of the annular outer surface of the tube member measured from the proximal open end to the distal open end of the tube member.

The apparatus and method of this invention provide for the treatment or prevention of many undesired side effects of endotracheal or tracheostomy tubes such as, for example, discomfort, violent coughing, gagging, increases in blood pressure, increases in heart rate, increases in intracranial pressures, surgical bleeding, hematoma, bronchospasm and airway swelling and inflammation.

Figure 3:
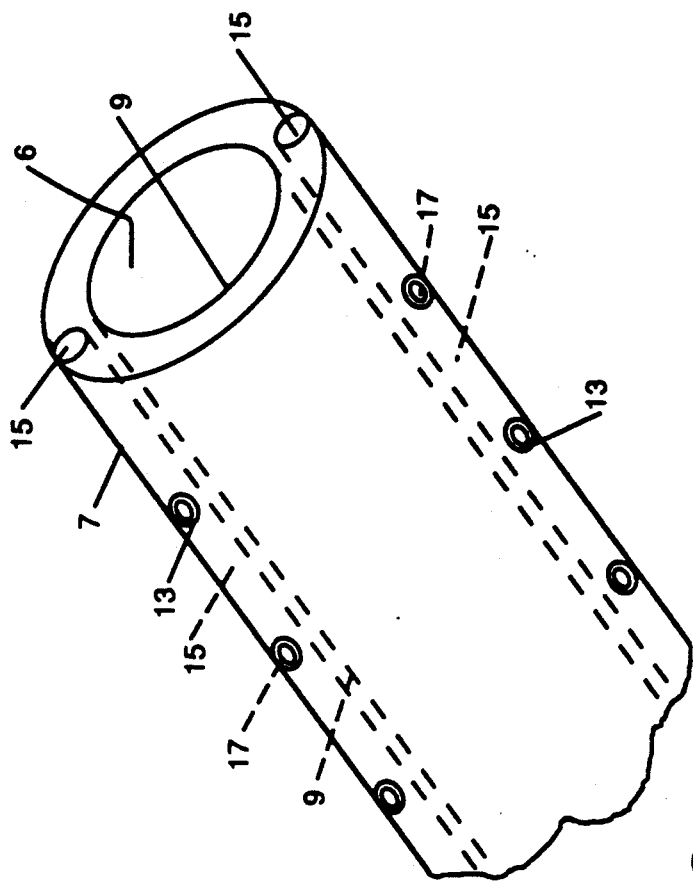
FIG. 3 is a schematic perspective view of the substantial alignment of the openings of the annular outer surface of the tube member and the perforations of the first conduit member.

FIGS. 1, 2 and 3 illustrate a preferred form of the apparatus of this invention for topical targeted delivery of a substance to the internal body tissues and walls of a patient's upper airway. In FIGS. 1 and 2, a tube member 1 has (a) a proximal open end 3 and a distal open end 5 and a central lumen 6 disposed between the proximal open end 3 and the distal open end 5 for ventilating or oxygenating the patient's lungs, and (b) an annular outer surface 7, and an annular inner surface 9. Tube member 1 may have a radius of curvature 11 as shown in FIG. 1. The radius of curvature may vary depending on the end use application of the apparatus. Preferably the radius of curvature 11 is from about 5 to 20 centimeters. FIG. 3 shows that the annular outer surface 7 has a plurality of openings 13 that are distributed and extend in a generally axial direction over a major portion of the axial extent of the annular outer surface 7. Preferably, openings 13 are uniformly distributed over a major portion of the axial extent of the annular outer surface 7. This apparatus includes at least one substance delivery means which includes at least two conduit members 15 positioned generally at least in part between the annular inner surface 9 and the annular outer surface 7. The conduit members 15 preferably extend over the major portion of the axial extent of the annular outer surface 7 of the tube member 1. Preferably, the conduit members 15 are positioned generally parallel to the longitudinal axis (not shown) of the tube member 1. The conduit members 15 have a plurality of perforations 17 that extend over substantially the length of conduit members 15 in substantial alignment with the openings 13 of the annular outer surface 7 of the tube member 1. The aligned openings 13 of the annular outer surface 7 and the perforations 17 of the conduit members 15 allow for a substance travelling within the conduit members 15 to flow through the aligned conduit member perforations 17 and the openings 13 of the annular outer surface 7 of the tube member 1 for delivery to the surrounding internal body tissues and walls of the patient's upper airway. FIG. 1 shows that this apparatus includes at least one supply means 19. Supply means 19 has a first end in communication with the conduit members 15 for delivering the substance to the conduit members 15. FIG. 1 shows a form of the apparatus of this invention wherein one supply means 19 communicates with two conduit members 15. It will be understood, however, that a supply means 19 may be provided to communicate with each conduit members 15. In addition, more than two conduit members may be provided in communication with each supply means 19. The supply means 19 is located so as to extend at least in part outside of the patient's body when the apparatus is inserted into the patient's airway. Supply means 19 has a second end in communication with an injection port 21 which accommodates, for example, a syringe, a pump or mechanical means (not shown) for effecting transfer of the substance from the syringe, pump or mechanical means into the supply means 19. The injection port 21 is positioned so as to extend outside of the patient's body when the apparatus is inserted into the patient's airway. Preferably, the supply means is a pipe 11.

It will be understood by those skilled in the art that the conduit members 15 may be positioned in regard to the longitudinal axis of tube member 1 in geometrical conformations other than the parallel arrangement described herein. For example, the conduit members 15 may be positioned generally in a spiral or helical arrangement in regard to the longitudinal axis of the tube member 1.

It will be understood that the general alignment of the perforations 17 of the conduit members 15 and the openings 13 of the annular outer surface 7 of the tube member 1 is of such an arrangement that the substance within the conduit members 15 is prevented from flowing into the central lumen 6 of the tube member 1.

It will be understood that the distal portion of the conduit members 15 ends in a manner such that the substance within the conduit members 15 exists the conduit members 15 outwardly and radially through the perforations 17 and the openings 13.

In a preferred embodiment of this invention, the substance delivery means of this apparatus includes two or more conduit members 15 generally uniformly and circumferentially spaced from each other and disposed at least in part between the annular inner surface 9 and the annular outer surface 7 of the tube member 1. It will be appreciated that such an arrangement provides for the delivery of a substance to substantially the entire mucosal lining and anatomical structures of the patient's upper airway. It is preferable that the tube member 1 be generally circular. Also, it is preferable that the conduit members 15 be generally circular. It will be appreciated, however, that the tube member 1 and the conduit members 15 may be various shapes such as, for example, oval or elliptical.

It will be appreciated by those skilled in the art that the distal open end of the tube member may have a slanted portion known as a bevel. The angle of the bevel is the angle between the bevel and the longitudinal axis of the tube member. The bevel angle may vary, for example, such as from about 30 to 60 degrees. Preferably, the bevel angle is from about 30 to 46 degrees. The bevel angle facilitates passage of the tube member into the patient's upper airway. Also, the distal end of the tube member may have an eye positioned opposite to the bevel. Such an eye is known by those skilled in the art as a Murphy eye. The purpose of the eye is to allow for ventilation or oxygenation of the patient's lungs if the bevel of the distal open end is occluded. Also, it will be appreciated by those skilled in the art that a radiopaque marker or other markings may be placed along at least part of the length of the longitudinal extent of the tube member to aid in determination of the distal open end position in the patient's upper airway after intubation.

The openings 13 of the annular outer surface 7 have a diameter of from about less than 1 millimeter to 2 millimeters. The conduit member perforations 17 have a diameter of from about less than 1 millimeter to 2 millimeters. In one form of this invention, it is preferable that openings 13 have generally a uniform size and that the conduit member perforations 17 have generally a uniform size. The openings 13 and the perforations 17 may be various shapes such as, for example, circular or elliptical. It will be understood that when the substance is a liquid, the size of these diameters may vary depending upon the viscosity of the substance to be delivered to the patient's upper airway.

In a form of this invention, the distribution of the perforations 17 and the openings 13 over the major portion of the axial extent of the tube member 1 is uniform. It will be appreciated by those skilled in the art that the size and shape of the perforations and openings, and the spacing or distance between each opening will determine the characteristics of the substance delivered to the mucosal lining and anatomical structures of the patient's upper airway. For example, smaller sized perforations 17 and openings 13 will allow substances delivered under pressure through the first member 15 to flow through the perforations 17 and openings 13 as a fine mist or atomized, nebulized or aerosol spray. Alternatively, larger sized openings 13 will allow delivery of the substance to the patient's upper airway as a bath or flush.

Preferably, conduit members 15 is fixedly positioned between the annular outer surface 7 and the annular inner surface 9 of the tube member 1.

The central lumen 6 of the tube member 1 has a diameter from about 1 to 12 millimeters. It will be appreciated by those skilled in the art that the diameter of central lumen 6 is dependent upon whether the apparatus will be inserted into the upper airway of a pediatric or adult patient. In a preferred embodiment of this invention, the lumen of the conduit members 15 has a diameter of about less than 1 millimeter. It is preferable that the tube member 1 is generally from about 5 to 20 centimeters in length from the distal open end to the proximal open end for pediatric human patients and from about 10 to 34 centimeters in length from the distal open end to the proximal open end for adult human patients.

It will be understood by those skilled in the art that a variety of sizes and shapes of endotracheal or tracheotomy tubes are available for specialized end use applications. It will be appreciated that the apparatus and methods of the present invention described herein may be adapted to these specialized end use applications.

Figure 4:
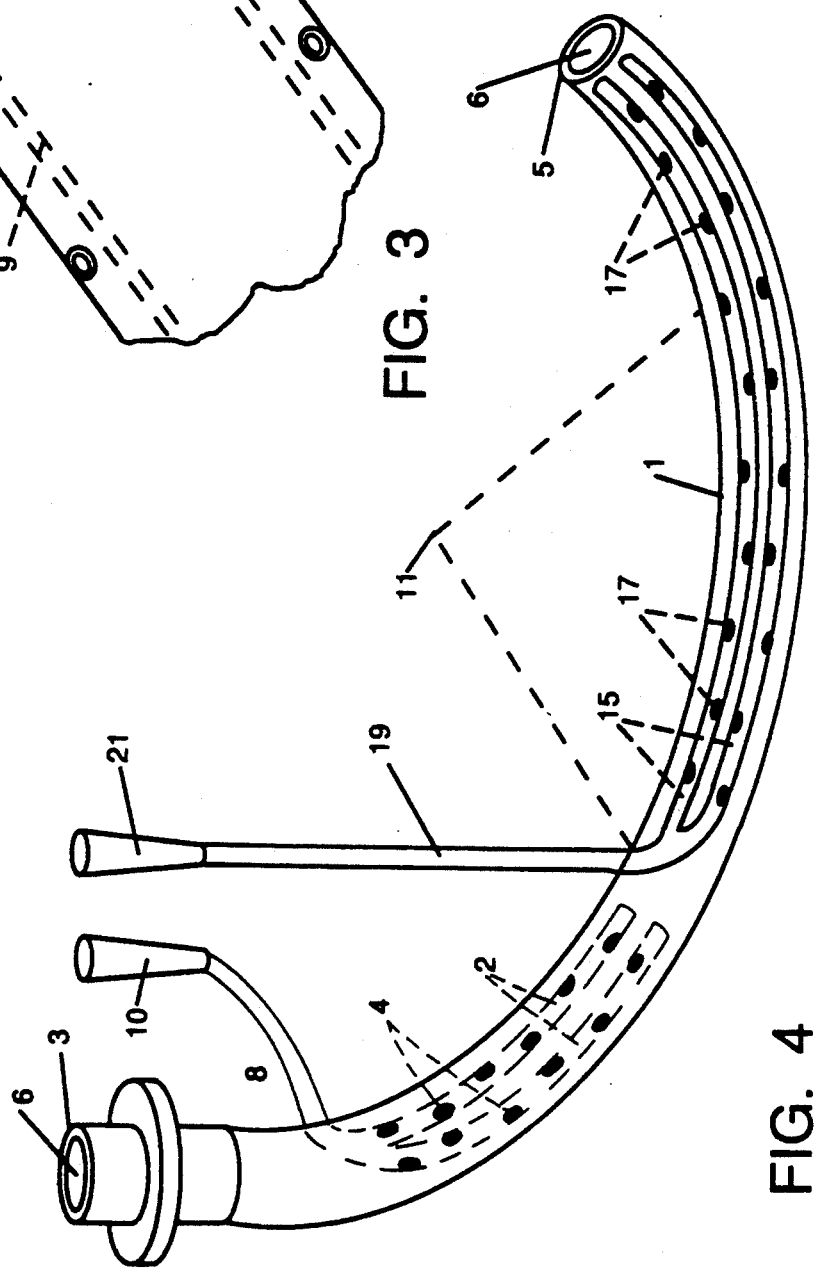
FIG. 4 is a schematic perspective of another embodiment of this apparatus including at least one second conduit member positioned generally at least in part between the annular inner surface and the annular outer surface of the tube member.

FIG. 4 shows a further embodiment of the hereinbefore described apparatus of this invention. In the embodiment shown in FIG. 4, at least two substance delivery means are provided. In addition to the substance delivery means that extends over the major portion of the axial extend to tube member 1, a second substance delivery means extends over a minor portion of the axial extent of tube member 1. Substance delivery means includes at least one conduit member 2 positioned generally at least in part between the annular inner surface 9 and the annular outer surface 7 of the tube member 1. The conduit member 2 extends over a minor portion of the axial extent of the annular outer surface 7 of the tube member 1. Preferably, the conduit member 2 is positioned generally parallel to the longitudinal axis (not shown) of the tube member 1. Conduit member 2 has a plurality of holes 4 or perforations that extend over the conduit member 2 in substantial alignment with the openings 13 of the annular outer surface 7 of the tube member 1. This alignment of the holes 4 of the conduit member 2 and the openings 13 of the annular outer surface 7 of the tube member 1 allow for a substance travelling within the conduit member 2 to flow through the aligned conduit member holes 4 and the openings 13 of the annular outer surface 7 of the tube member 1 to the surrounding uppermost mucosal lining and anatomical structures of the patient's upper airway.

FIG. 4 shows that substance delivery means includes at least one supply means 8. Supply means 8 has a first end in communication with the conduit member 2 for delivering the substance to the conduit member 2. The supply means 8 is located so as to extend at least in part outside of the patient's body when the apparatus is inserted into the patient's airway. Supply means 8 has a second end in communication with an injection port 10 which accommodates, for example, a syringe, a pump or mechanical means (not shown) for effecting transfer of the substance from the syringe, pump or mechanical means into the supply means 8. The injection port 10 is located so as to extend outside of the patient's body when the apparatus is inserted into the patients airway. Preferably, the supply means 8 is a pipe. FIG. 4 shows a form of the apparatus wherein one supply means 8 communicates with two conduit members 2. It will be understood, however, that a supply means 8 may be provided to communicate with each conduit member 2. It is preferable when employing two or more conduit members 2 that each conduit member is generally uniformly circumferentially spaced from each other.

It will be appreciated by those skilled in the art that the conduit member 2 may be positioned in regard to the longitudinal axis of tube member 1 in geometrical conformations other than the parallel arrangement described herein.

FIGS. 5 and 6 show another embodiment of this invention. In FIGS. 5 and 6, a tube member 1 has (a) a proximal open end 3, a distal open end 5, and a central lumen 6 disposed between the proximal open end 3 and the distal open end 5 for ventilating or oxygenating the patient's lungs, and (b) an annular outer surface 7 and an annular inner surface 9. FIG. 5 shows that tube member 1 has a radius of curvature 11.

In FIGS. 5 and 6, at least one passageway 20 is fixedly positioned on the annular outer surface 7 of the tube member 1. Passageway 20 extends over the major portion of the axial extent of the annular outer surface 7 of the tube member 1. Preferably, passageway 20 is positioned generally parallel to the longitudinal axis (not shown) of the tube member 1. Passageway 20 has a plurality of apertures 22 that extend over the axial extent of passageway 20. The apertures 22 allow a substance to flow from within passageway 20 through the apertures to the surrounding internal body tissues and walls of the patient's upper airway.

FIG. 5 shows that at least one supply means 24 has a first end in communication with the passageway 20 for delivering the substance to the passageway 20. The supply means 24 is located so as to extend at least in part outside of the patient's body when the apparatus is inserted into the patient's airway. Supply means 24 has a second end in communication with injection port 26 which accommodates, for example, a syringe, a pump or mechanical means (not shown) for effecting transfer of the substance from the syringe, pump or mechanical means into the supply means 24. The injection port 26 is located so as to extend outside of the patient's body when the apparatus is inserted into the patient's airway. Preferably, the supply means 24 is a pipe.

FIG. 6 shows an embodiment having two passageways 20 generally circumferentially spaced from one another. It will be appreciated that any number of passageways 20 may be provided.

It will be understood that passageways 20 may be positioned in regard to the longitudinal axis of tube member 1 in geometrical conformations other than the parallel arrangement described herein.

In another embodiment of this invention, the apparatus includes at least one inflatable balloon cuff member 23 as shown in FIG. 7. Inflatable balloon cuff member 23 is attached to and continuously or entirely encircles at least part of the axial extent of tube member 1 for sealing engagement against the internal body tissues and walls of the patient's upper airway. FIG. 8 shows that at least one inflation conduit member 25 is positioned generally at least in part between the annular outer surface 7 and the annular inner surface 9 of the tube member. Inflation conduit member 25 has a first end in communication with the inflatable balloon cuff member 23. Inflation conduit member 25 extends over the major portion of the axial extent of the annular outer surface 7 of the tube member 1. Preferably, the inflation conduit member 25 is positioned generally parallel to the longitudinal axis (not shown) of the tube member 1. At least one inflation air supply means 27 has a first end in communication with a second end of the inflation conduit member 25 for transferring air or other fluid to the inflation conduit member 25 for inflating the inflatable balloon cuff member 23 and effecting sealing engagement of the inflatable balloon cuff member 23 against the internal body tissues and walls of the patient's upper airway. It will be appreciated by those skilled in the art that effecting sealing engagement of the inflatable balloon cuff member 23 against the walls of the patient's upper airway resists the upward escape through the trachea externally of the tube member 1 of oxygen or a gaseous anesthetic administered by way of the central lumen 6 of tube member 1 and directed to the patient's lungs. Also, sealing engagement of the inflatable balloon cuff member 23 against the walls of the patient's upper airway resists the passage of secretions and vomitus around tube member 1 and into the patient's lungs. Inflation air supply means 27 is located so as to extend at least in part outside of the patient's body when the apparatus is inserted into the patient's airway. Inflation air supply means 27 has a second end in communication with inflation air injection port 29 which accommodates, for example, a syringe, a pump or mechanical means for forcing air into and through the inflation air supply means 27 and the inflation conduit member 25 to inflate the inflatable balloon cuff member 23. It will be understood that the inflated inflatable balloon cuff member 23 may be deflated by permitting the air to travel out of inflatable balloon cuff member 23 and through the inflation conduit member 25, the inflation air supply means 27 and the inflation air injection port 29. Inflation air supply means 27 may include a pilot balloon 31 disposed generally below the inflation air injection port 29 for monitoring the extent of inflation of inflatable balloon cuff member 23.

It will be understood that the area between the annular inner surface and the annular outer surface of the tube member is generally a solid region but for the conduits or passageways, as hereinbefore defined, disposed between the annular inner and outer surfaces. It will be appreciated, however, that the area between the annular outer and inner surfaces may be a hollow region.

It will be understood that the injection ports, as hereinbefore defined, may include valve means for effecting the transfer of the substance. It will be understood that the inflation air injection port may include valve means for effecting the inflation and deflation of the inflatable balloon cuff member.

It is well known by those skilled in the art that topical applications of local anesthetic solutions may be applied to the upper airway prior to insertion of the endotracheal or tracheostomy tube by a variety of mechanisms including, for example, sprays, inhaled aerosols and injections. Applying these topical applications of anesthetics prior to insertion has been established as a generally safe and very effective method of preventing discomfort, coughing, gagging and elevation of blood pressure, heart rate and intracranial pressure from occurring during the insertion of the endotracheal or tracheostomy tube. However, once the endotracheal or tracheostomy tube is in place, it has not been possible heretofore to spray substantially the entire length of the patient's upper airway mucosal lining with local anesthetic solution.

In another embodiment of this invention, a method is provided for administering or spraying a substance, including for example, a local anesthetic solution, to substantially the entire length of the mucosal lining and anatomic structures of the patient's upper airway. This method includes employing the hereinbefore described apparatus of this invention, inserting at least part of the apparatus of this invention into the upper airway through the patient's nose or mouth and down into the trachea or directly into the larynx or trachea to secure and protect the upper airway and to permit the safe and proper life-sustaining ventilation or oxygenation of the patient's lungs, injecting a substance into the injection port for transfer of the substance through the supply means and into at least one of the conduit members, and effecting the flow of the substance through a plurality of the aligned conduit member perforations and the openings of the annular outer surface for the delivery of the substance to generally the entire mucosal lining and anatomical structures of the patient's upper airway.

It will be appreciated that after the desired treatment is accomplished, this method includes removing the apparatus of this invention from the patient's upper airway after effecting the delivery of the substance to the mucosal lining and anatomical structures of the patient's upper airway.

In another embodiment of this invention, a method is provided for the topical delivery of a substance to generally the entire mucosal lining and anatomical structures of a patient's upper airway and selected portions thereof which includes employing the hereinbefore described apparatus of this invention; inserting at least part of the apparatus into the patient's upper airway, injecting the substance into at one of (1) a first injection port which communicates with the first supply means for the transfer of the substance through the first supply means and into at least one first conduit member which extends along a major portion of the axial extent of the tube member, and (2) a second injection port which communicates with the second supply means for the transfer of the substance through the second supply means and into at least one second conduit member which extends along a minor portion of the axial extent of the tube member; and effecting the flow of the substance through a plurality of at least one of (1) aligned first conduit member perforations and the openings of the annular outer surface for delivery of the substance to generally the entire mucosal lining and anatomical structures of the patient's upper airway adjacent to a major portion of the axial extent of the tube member, and (2) the aligned second conduit member perforations and the openings of the annular outer surface for delivery of the substance to generally the uppermost mucosal lining and anatomical structures of the patient's upper airway adjacent to a minor portion of the axial extent of the tube member.

In another embodiment of this invention, a method is provided for the topical delivery of a substance to generally the entire mucosal lining and anatomical structures of a patient's upper airway which includes employing the hereinbefore described apparatus of this invention, inserting at least part of the apparatus into the patient's upper airway, injecting the substance into an injection port which communicates with the supply means for transfer of the substance through the supply means and into at least one passageway, and effecting the flow of the substance through a plurality of the apertures for delivery of the substance to generally the entire mucosal lining and anatomical structures of the patient's upper airway.

It will be appreciated by those skilled in the art that the method of this invention provides for a local anesthetic to be delivered generally to the uppermost mucosal lining and anatomical structures of the upper airway or to the entire mucosal lining of the upper airway by way of the substantially aligned conduit member perforations or holes and the openings of the annular outer surface and/or the apertures of the passageway extending along major and/or minor portions of the axial extent of the tube member. It will also be appreciated by those skilled in the art that, depending on the size and arrangement of these perforations and openings and/or apertures, as hereinbefore described, a fine mist or spray is delivered and directed to selected portions of or the entire mucosal lining and anatomical structures of the patient's upper airway.

It will also be understood by those skilled in the art that the method of this invention may include inserting the hereinbefore described apparatus into the trachea wherein the apparatus includes the inflatable balloon cuff member. If the apparatus includes the inflatable balloon cuff member, the method includes inflating the inflatable balloon cuff member after inserting the apparatus into the patient's upper airway. It will be appreciated that the inflatable balloon cuff member may be transiently partially deflated to permit the portion of the trachea in contact with the inflatable balloon cuff member to be sprayed or bathed with the substance as well.

It will be appreciated by those skilled in the art that this invention provides an apparatus and method for direct topical targeted delivery of a substance to generally the entire or selected portions of the mucosal lining and anatomical structures of the upper airway of an intubated patient. The apparatus and method advantageously provide for the treatment and prevention of the undesired side effects of maintaining and removing an endotracheal or tracheostomy tube from the upper airway.

Whereas particular embodiments of the invention have been described herein for purpose of illustration, it will be evident to those skilled in the art that numerous variations of the details of the present invention may be made without departing from the invention as defined in the appended claims.

What is claimed is:

1. An apparatus for topical targeted delivery of a substance to the surrounding internal body tissues and walls of a patient's upper airway which comprises:

a tube member having (a) a proximal open end, a distal open end, and a central lumen for oxygenating or ventilating the lungs of the patient, said central lumen disposed between said proximal open end and said distal open end, and (b) an annular outer surface having a plurality of openings therein, and an annular inner surface, said openings of said annular outer surface extending over at least a portion of the axial extent of said annular outer surface of said tube member positioned to be surrounded by internal body tissues and walls of the patient's upper airway when inserted into the patient's upper airway; and at least one substance delivery means in communication with said tube member, each said substance delivery means including at least two conduit members disposed generally at least in part between said annular inner surface and said annular outer surface, wherein said conduit members extend over said portion of the axial extent of said annular outer surface of said tube member positioned to be surrounded by internal body tissues and walls of the patient's upper airway when inserted into the patient's upper airway, a plurality of conduit member perforations extending over each said conduit member in substantial alignment with said openings of said annular outer surface of said tube member to facilitate communication therebetween for allowing the substance travelling through said conduit members to flow from within said conduit members by passing through said conduit member perforations and said openings of said annular outer surface of said tube member to be delivered to said surrounding internal body tissues and walls of said airway, and supply means having a first end in communication with said conduit members, for delivering said substance to said conduit members.

2. The apparatus of claim 1 wherein said conduit members are positioned generally parallel to the longitudinal axis of said tube member.

3. The apparatus of claim 1 wherein said openings of said annular outer surface are generally uniformly distributed and said conduit member perforations are generally uniformly distributed and are disposed over said conduit member in substantial alignment with said openings of said annular outer surface.

4. The apparatus of claim 3 wherein said conduit members are at least in part fixedly secured between said annular outer surface and said annular inner surface.

5. The apparatus of claim 4 wherein said conduit members are generally uniformly circumferentially spaced from each other.

6. The apparatus of claim 5 wherein said tube member has a radius of curvature of from about 5 to 20 centimeters.

7. The apparatus of claim 6 wherein said openings of said annular outer surface have a diameter of from about less than 1 millimeter to 2 millimeters.

8. The apparatus of claim 7 wherein said first conduit member perforations have a diameter of from about less than 1 millimeter to 2 millimeters.

9. The apparatus of claim 8 wherein said central lumen of said tube member has a diameter from about 1 to 12 millimeters.

10. The apparatus of claim 9 wherein the lumen of said first conduit member has a diameter of about less than 1 millimeter.

11. The apparatus of claim 10 wherein said tube member is generally from about 5 to 34 centimeters in length from said proximal open end to said distal open end.

12. The apparatus of claim 5 wherein said openings of said annular outer surface have generally a uniform size.

13. The apparatus of claim 12 wherein said conduit member perforations have generally a uniform size.

14. The apparatus of claim 12 wherein said supply means is adapted to be positioned so that at least a portion thereof will extend outside of the patient's body.

15. The apparatus of claim 14 wherein said supply means has a second end in communication with an injection port and located on said portion extending outside of the patient's body.

16. The apparatus of claim 15 wherein said first supply means is a pipe.

17. The apparatus of claim 1 wherein said distal open end is a bevel.

18. The apparatus of claim 17 wherein said distal open end has an eye positioned opposite said bevel.

19. The apparatus of claim 1 including at least one inflatable balloon cuff member attached to and continuously encircles at least part of the axial extent of said tube member for sealing engagement against the internal body tissues and walls of the patient's upper airway.

20. The apparatus of claim 19 including at least one inflation conduit member positioned generally at least in part between said annular inner surface and said annular outer surface, said inflation conduit member having a first end in communication with said inflatable balloon cuff member and extends over a portion of the axial extent of said annular outer surface of said tube member.

21. The apparatus of claim 20 wherein said inflation conduit member is positioned generally parallel to the longitudinal axis of said tube member.

22. The apparatus of claim 20 including an inflation air supply means having a first end in communication with a second end of said inflation conduit member for transferring air to said inflation conduit member for effecting sealing engagement of said inflatable balloon cuff member against the internal body tissues and walls of the patient's upper airway.

23. The apparatus of claim 22 wherein said inflation air supply means is adapted to be positioned so that at least a portion thereof will extend outside of the patient's body.

24. The apparatus of claim 23 wherein said inflation air supply means has a second end in communication with an inflation air injection port through which air may be forced into and through said inflation air supply means and said inflation conduit member for effecting the inflation of said inflatable cuff member, said inflation air injection port being adapted to be positioned to extend outside of the patient's body.

25. The apparatus of claim 24 wherein said inflation air supply means has a pilot balloon disposed generally below said inflation air injection port, said pilot balloon is adapted to be located outside of the patient's body.

26. The apparatus of claim 1 wherein said tube member is generally circular.

27. The apparatus of claim 26 wherein said conduit members are generally circular.

28. The apparatus of claim 1 wherein at least one said substance delivery means includes at least two said conduit members extending over a major portion of the axial extent of said annular outer surface of said tube member.

29. The apparatus of claim 1 wherein at least one said substance delivery means includes at least two said conduit members extending over a minor portion of the axial extent of said annular outer surface of said tube member.

30. A method for topical delivery of a substance to generally the entire mucosal lining and anatomical structures of a patient's upper airway which comprises:
providing an apparatus which comprises (1) a tube member having (a) a proximal open end, a distal open end and a central lumen disposed between said proximal open end and said distal open end for ventilating or oxygenating the patient's lungs, and (b) an annular outer surface having a plurality of openings therein, and an annular inner surface; (2) at least one substance delivery means in communication with said tube member, each said substance delivery means having (a) at least two conduit members disposed generally at least in part between said annular inner surface and said annular outer surface, (b) a plurality of conduit member perforations disposed over each said first conduit members in substantial alignment and communication with said openings of said annular outer surface of said tube member, (c) supply means having a first end in communication with said conduit members for delivering said substance to said conduit members, and (d) an injection port which communicates with said supply means;
inserting at least part of said apparatus into the patient's upper airway;
injecting said substance into at least one said injection port for transfer of said substance through said supply means and into at least one substance delivery means; and
effecting the flow of said substance through a plurality of the aligned said conduit member perforations and said openings of said annular outer surface for delivery of said substance to generally the entire mucosal lining and anatomical structures of the patient's upper airway.

31. The method of claim 30 including removing said apparatus from the patient's upper airway after effecting the delivery of said substance to the mucosal lining and anatomical structures of the patient's upper airway.

32. The method of claim 30 including providing said apparatus having at least one said conduit member positioned generally parallel to the longitudinal axis of said tube member.

33. The method of claim 30 including providing said apparatus wherein said tube member is generally circular.

34. The method of claim 33 including providing said apparatus wherein at least one said conduit member is generally circular.

35. The method of claim 30 including providing said apparatus wherein each said delivery means includes at least two said conduit members generally uniformly circumferentially spaced from each other.

36. The method of claim 30 including providing said apparatus wherein said openings of said annular outer surface have generally a uniform size.

37. The method of claim 36 including providing said apparatus wherein said conduit member perforations have generally a uniform size.

38. The method of claim 30 including providing an inflatable balloon cuff member which is attached to and continuously encircles at least part of the axial extent of said tube member; and
inflating said inflatable balloon cuff member for sealing engagement of said inflatable balloon cuff member against said mucosal lining and anatomical structures of said upper airway before injecting said substance into said first injection port.

39. The method of claim 38 including transiently partially deflating said inflatable balloon cuff member while effecting said flow of said substance to permit the portion of said upper airway in contact with said inflatable balloon cuff member to be bathed or sprayed with said substance.

40. The method of claim 39 including deflating said inflatable balloon cuff member and then removing said apparatus from the patient's upper airway after effecting the delivery of said substance.

41. The method of claim 30, including employing said apparatus wherein at least one said substance delivery means extends over a major portion of the axial extent of said tube member.

42. The method of claim 41, including employing said apparatus wherein at least one said substance delivery means extends over a minor portion of the axial extent of said tube member.

* * * * *